United States Patent
Wan et al.

(10) Patent No.: US 10,022,373 B2
(45) Date of Patent: Jul. 17, 2018

(54) POSACONAZOLE PHARMACEUTICAL COMPOSITIONS AND PREPARATION METHODS, USES AND PHARMACEUTICAL FORMULATIONS THEREOF

(71) Applicant: SINOTHERAPEUTICS INC., Shanghai (CN)

(72) Inventors: Jiansheng Wan, Shanghai (CN); Kun Li, Shanghai (CN); Xiaoxi Sheng, Shanghai (CN)

(73) Assignee: SINOTHERAPEUTICS INC., Shanghai (CN)

( * ) Notice: Subject to any disclaimer, the term of this patent is extended or adjusted under 35 U.S.C. 154(b) by 0 days.

(21) Appl. No.: 15/303,389

(22) PCT Filed: Apr. 10, 2015

(86) PCT No.: PCT/CN2015/076299
§ 371 (c)(1),
(2) Date: Oct. 11, 2016

(87) PCT Pub. No.: WO2015/154718
PCT Pub. Date: Oct. 15, 2015

(65) Prior Publication Data
US 2017/0027931 A1 Feb. 2, 2017

(30) Foreign Application Priority Data

Apr. 11, 2014 (CN) .......................... 2014 1 0145747

(51) Int. Cl.
| | | |
|---|---|---|
| *A61K 31/473* | (2006.01) | |
| *A61K 31/496* | (2006.01) | |
| *A61K 47/32* | (2006.01) | |
| *A61K 47/34* | (2017.01) | |
| *A61K 47/38* | (2006.01) | |

(52) U.S. Cl.
CPC ............ *A61K 31/496* (2013.01); *A61K 47/32* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 2003/0108616 A1* | 6/2003 | Bosch | ..................... | A61K 9/145 424/497 |
| 2007/0281011 A1* | 12/2007 | Jenkins | ..................... | A61K 9/14 424/464 |
| 2011/0123627 A1* | 5/2011 | Fang | ..................... | A61K 9/1652 424/489 |
| 2015/0231081 A1* | 8/2015 | Kulkarni | .............. | A61K 31/496 514/254.07 |

FOREIGN PATENT DOCUMENTS

| | | |
|---|---|---|
| CN | 101495096 A | 7/2009 |
| CN | 101951891 A | 1/2011 |
| CN | 102665762 A | 9/2012 |
| CN | 102906169 A | 1/2013 |
| CN | 104510707 A | 4/2015 |
| CN | 104546667 A | 4/2015 |
| JP | 2011518140 A | 6/2011 |
| WO | 2009087410 A2 | 7/2009 |
| WO | 2009127825 A1 | 10/2009 |
| WO | 2011064111 A1 | 6/2011 |
| WO | 2011144731 A1 | 11/2011 |
| WO | 2012151237 A1 | 11/2012 |
| WO | 2015/148483 | * 10/2015 |

OTHER PUBLICATIONS

International Search Report dated Jul. 15, 2015, in PCT/CN2015/076299, with English translation, 6 pages.
Japanese Office Action dated Sep. 5, 2017, in JP 2017-504231, 5 pages.
Chinese Office Action dated Jun. 1, 2017, in CN 201410145747.6, 8 pages.
Dinunzio, J. C., et al., "Chapter 9: Melt Extrusion," In re R. O. Williams III et al. (Eds.) Formulating Poorly Water Soluble Drugs, 2012, 311-361.
Shah, S., et al., "Melt extrusion with poorly soluble drugs," International Journal of Pharmaceutics, 453, 2013. 233-252.
Linn, M., et al., "Soluplus as an effective absorption enhancer of poorly soluble drugs in vitro and in vivo," European Journal of Pharmaceutical Sciences, 45, 2012, 336-343.
Verreck, G., et al., "The effect of pressurized carbon dioxide as a temporary plasticizer and foaming agent on the hot stage extrusion process and extrudate properties of solid dispersions of itraconazole with PVP-VA 64," European Journal of Pharmaceutical Sciences, 26, 2005, 349-358.
Wang, X., et al., "Solid state characteristics of ternary solid dispersions composed of PVP VA64, Myrj 52 and itraconazole," International Journal of Pharmaceutics, 303, 2005, 54-61.
Zhang, K., et al., "Increased dissolution and oral absorption of itraconazole/Soluplus extrudate compared with itraconazole nanosuspension," European Journal of Pharmaceutics and Biopharmaceutics, 2013, http://dx.doi.org/10.1016/j.ejpb.2013.03. 002, 8 pages.

* cited by examiner

*Primary Examiner* — Karl J Puttlitz
(74) *Attorney, Agent, or Firm* — Rothwell, Figg, Ernst & Manbeck, P.C.

(57) ABSTRACT

The present invention relates to a pharmaceutical composition comprising posaconazole and a carrier material, wherein the carrier material comprises a vinylpyrrolidone-vinyl acetate copolymer or a polymer containing ethylene glycol units. The present invention also relates to a method for the preparation of the pharmaceutical composition, a method for the prevention and/or treatment of fungal infections and related diseases in a mammal using the pharmaceutical composition, and a pharmaceutical formulation comprising the pharmaceutical composition.

13 Claims, 3 Drawing Sheets

POSACONAZOLE PHARMACEUTICAL COMPOSITIONS AND PREPARATION METHODS, USES AND PHARMACEUTICAL FORMULATIONS THEREOF

CROSS REFERENCE TO RELATED APPLICATION(S)

This application is a 35 U.S.C. § 371 National Phase Entry Application from PCT/CN2015/076299, filed Apr. 10, 2015, designating the United States, which claims priority under 35 U.S.C. § 119 to Chinese patent application 201410145747.6, filed Apr. 11, 2014, the entire disclosure of which is incorporated herein by reference.

FIELD OF THE INVENTION

The present invention relates to pharmaceutical compositions and preparation methods, uses and pharmaceutical formulations thereof. In particular, the present invention relates to pharmaceutical compositions comprising posaconazole as an active ingredient, methods for the preparation of the pharmaceutical compositions, methods for the prevention and/or treatment of fungal infections and related diseases in mammals using the pharmaceutical compositions, and pharmaceutical formulations comprising the pharmaceutical compositions.

BACKGROUND OF THE INVENTION

Posaconazole is a derivative of itraconazole, and belongs to the second-generation triazole antifungal agents. It has the chemical name of 4-[4-[4-[4-[[(3R,5R)-5-(2,4-difluorophenyl)-5-(1,2,4-triazole-1-ylmethyl)oxolan-3-yl]methoxy]phenyl]piperazin-1-yl]phenyl]-2-[(2S,3S)-2-hydroxypentan-3-yl]-1,2,4-triazol-3-one, and has the structural formula

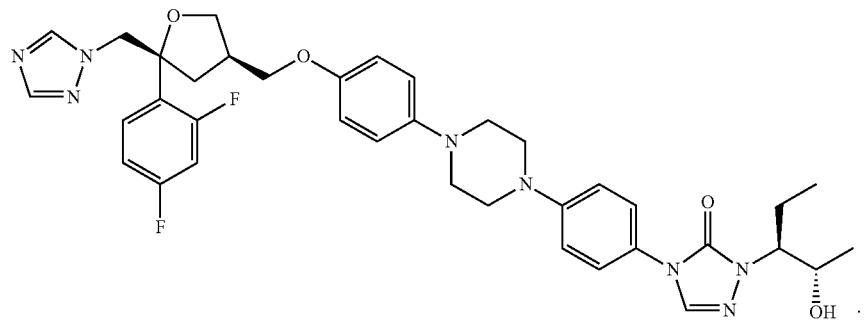 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

U.S. Pat. No. 5,703,079 and U.S. Pat. No. 5,661,151, the disclosures of which in their entireties are hereby incorporated by reference into this application, disclose posaconazole and its synthetic method, respectively.

Posaconazole overcomes the problems of the first-generation triazole antifungal agents, i.e. narrow antibacterial spectrum, low bioavailability, drug resistance, etc., and has the characteristic of broad antibacterial spectrum. Posaconazole can prevent invasive aspergillosis more effectively by comparison with fluconazole and itraconazole, and can reduce the mortality rate in relation to invasive fungal infections.

A suspension containing posaconazole (40 mg/ml) in a crystalline form, Noxafil®, has been approved for the treatment of invasive fungal infections such as oropharyngeal candidiasis, including infections resistant to treatments with other azole antifungal agents, and for the prophylactic treatment of fungal infections in patients greatly susceptible to such infections due to severe immunodeficiency, such as hematopoietic stem cell transplantation (HSCT) receptors suffering from graft versus-host diseases (GVHD), or patients suffering from hematological malignances and having permanent leucopenia resulting from chemotherapy.

However, provision of pharmaceutical compositions comprising posaconazole suitable for the preparation of oral solid dosage forms has heretofore been hampered by the weak basicity and low solubility of posaconazole in free base form. Posaconazole has pKa values of 3.6 (piperazine) and 4.6 (triazole), and is slightly soluble at low pH. For example, in the environment of the stomach (pH=~1.2), posaconazole in free base form has a solubility of about 0.8 mg/ml. However, when pH is higher than 4, posaconazole is practically insoluble (solubility <~1 μg/ml). Therefore, when posaconazole dissolved in gastric fluid reaches the environment of the intestinal tract (typically, pH is or is higher than about 6.4) upon gastric emptying, the dissolved posaconazole crystallizes out, and thus the absorption of posaconazole is reduced and the bioavailability thereof is influenced.

US2011123627A discloses a posaconazole pharmaceutical composition comprising an enteric carrier material, the polymer hydroxypropylmethyl cellulose acetate succinate (HPMCAS), such that posaconazole is essentially insoluble when passing through stomach, but can be easily released upon entry into small intestine. This pharmaceutical composition improves the maximum plasma drug concentration and bioavailability of posaconazole in vivo by comparison with commercially available posaconazole oral suspensions. This pharmaceutical composition, however, limits the release of posaconazole in stomach, resulting in a delayed peak time ($T_{max}$) of plasma drug concentration in vivo. In addition, a posaconazole pharmaceutical composition prepared by hot melt extrusion using HPMCAS as a carrier material has high hardness, leading to difficulties in grinding. Also, the pharmaceutical composition has poor compressibility, bringing difficulties in subsequent processing such as tableting.

SUMMARY OF THE INVENTION

The object of the invention is to provide posaconazole pharmaceutical compositions that overcome the above-mentioned defects in the prior art.

In a first aspect of the present invention, there is provided a pharmaceutical composition comprising posaconazole and a carrier material, wherein the carrier material comprises a vinylpyrrolidone-vinyl acetate copolymer or a polymer containing ethylene glycol units. The pharmaceutical composition can be used for the prevention and/or treatment of fungal infections and related diseases in a mammal.

In a second aspect of the present invention, there is provided use of a pharmaceutical composition according to the first aspect of the invention in the manufacture of a medicament for the prevention and/or treatment of fungal infections and related diseases in a mammal.

In a third aspect of the present invention, there is provided a method for the prevention and/or treatment of fungal infections and related diseases in a mammal, comprising administering an effective amount of a pharmaceutical composition according to the first aspect of the invention to the mammal.

In a fourth aspect of the present invention, there is provided a method for the preparation of a pharmaceutical composition according to the first aspect of the invention, comprising:

preheating a hot melt extruder to 120° C.-180° C.;
feeding a homogeneously-mixed stoichiometric mixture of posaconazole, a carrier material, and optionally one or more pharmaceutically acceptable excipients into the hot melt extruder, or stoichiometrically feeding posaconazole, a carrier material, and optionally one or more pharmaceutically acceptable excipients into the hot melt extruder directly;
extruding; and
cooling, pulverizing and sieving the extrudate, optionally mixing it with one or more pharmaceutically acceptable excipients, thereby obtaining the pharmaceutical composition.

In a fifth aspect of the present invention, there is provided a pharmaceutical formulation in the form of a powder, a granule, a pill, a capsule or a tablet, comprising the pharmaceutical composition according to the first aspect of the invention.

DESCRIPTION OF DRAWINGS

The object and characteristics of the present invention will become more apparent with reference to the drawings, in which.

DETAILED DESCRIPTION OF THE INVENTION

Figure 1:
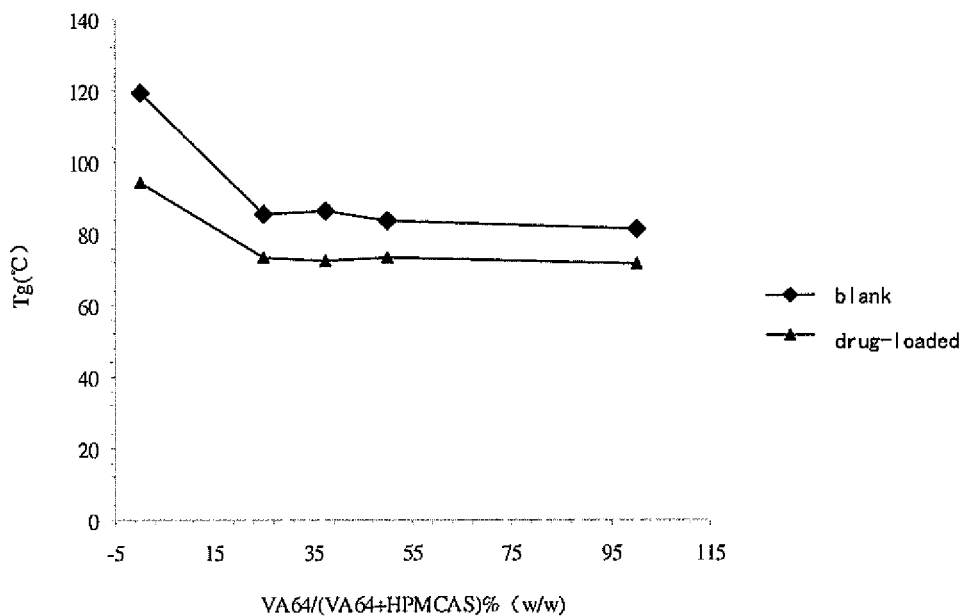
FIG. 1 shows the effect of VA64 content on Tg value in a pharmaceutical composition prepared with posaconazole—Kollidon® VA64 and/or HPMCAS carrier(s), wherein Tg values corresponding to VA64(VA64+HPMCAS)% of 0%, 25%, 37.5%, 50% and 100% are those of Composition 2-1, Composition 2-2, Composition 2-3, Composition 2-4, and Composition 1-3 or the corresponding blank compositions, respectively.

Unless defined otherwise, all the technical and scientific terms used herein have the same meanings as commonly known by a person skilled in the art. In case of confliction, the definitions provided herein will prevail.

When a certain value, concentration, or the like, or a parameter is expressed in the form of a range, a preferred range, or a preferred upper limit and a preferred lower limit, it shall be appreciated that it equals to disclosure of any range obtained by combining any of the upper limits or preferred values with any of the lower limits or preferred values, regardless whether the range is specifically disclosed or not. Unless indicated otherwise, it is intended that a numerical range recited herein encompasses the end points, as well as all the integers and fractions within the range.

The terms "about" and "approximate", when used along with a numerical variable, generally means the value of the variable and all the values of the variable within an experimental error (e.g. 95% confidence interval for the mean) or within a specified value ±10% or within a broader range.

The term "stoichiometric" means that substances are used in a certain weight ratio. For example, in the present invention, the API (posaconazole), the carrier material and the optional pharmaceutically acceptable excipient(s) are used in a certain weight ratio.

The term "pharmaceutically acceptable" substances means those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutical composition" means substances composed of one or more active ingredients, carriers and optionally one or more pharmaceutically acceptable excipients. In the present invention, it can be simply referred to as "composition". For example, Pharmaceutical Composition 1-1 can be simply referred to as Composition 1-1.

The term "blank composition" is relative to a pharmaceutical composition, and means that it comprises no active ingredient (i.e. posaconazole) and only comprises a carrier material and optionally one or more other pharmaceutically acceptable excipients.

The terms "pharmaceutical product", "pharmaceutical dosage form", "dosage form", "pharmaceutical formulation", etc., refer to a pharmaceutical composition administered to a patient in need of treatment, which is typically in the form of a powder, a granule, a pill, a capsule, a tablet, a solution, a suspension, or a patch, etc.

The term "dissolved in or dispersed at a molecular level in a (the) carrier material" means that a drug is dispersed in a (the) carrier material to form a single-phase pharmaceutical composition. In the present invention, this term means that posaconazole is dispersed in the carrier material to form a single-phase pharmaceutical composition (also referred to as a solid solution, a suspension, or a solid suspension). The Tg value of the resulting posaconazole pharmaceutical composition is different from those of the carrier material and the API posaconazole. The terms "dissolved in", "dispersed at a molecular level", "dispersion", "solid solution" and "solid dispersion" are used herein as appropriate to describe a pharmaceutical composition according to the invention in various stages during preparation and at various temperatures.

The term "bioavailability" indicates the extent to which a drug or another substance is utilized by a target tissue after administration.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0-\infty}$," means the area under a plasma drug concentration—time curve from the time point of 0 to infinity after drug administration, and the term "$AUC_{0-t}$" means the area under a plasma drug concentration—time curve from the time point of 0 to t after drug administration.

Unless specified otherwise, all the percentages, portions and ratios in the present invention are on weight basis.

The present invention provides a posaconazole pharmaceutical composition. The pharmaceutical composition according to the invention improves the absorption behavior of posaconazole in human body, and increases the absorption and bioavailability of the drug by comparison with the prior art. Further, the pharmaceutical composition according to the invention is prepared by a hot melt extrusion process, which is simple and easy to operate, and improves technique, decreases energy consumption, and increases productivity by comparison with the prior art.

Specifically, the inventors have found that a pharmaceutical composition wherein posaconazole is dissolved or dispersed at a molecular level in a carrier material can be prepared by processing a vinylpyrrolidone-vinyl acetate copolymer of a certain ratio, as a carrier material, and posaconazole with a hot melt extrusion process according to the invention. The inventors have found surprisingly that a pharmaceutical composition wherein posaconazole is dispersed in a vinylpyrrolidone-vinyl acetate copolymer can increase the solubility of posaconazole in gastrointestinal tract, and can ameliorate the problem of precipitation or crystallization due to the significant decrease of solubility resulting from the pH change upon entry of posaconazole dissolved in stomach into intestinal tract through gastric emptying, thereby increasing the absorption of posaconazole in vivo and the bioavailability thereof. In another aspect, the pharmaceutical composition can also alter the absorption behavior of posaconazole in vivo, increasing $C_{max}$ and AUC without prolonging $T_{max}$. Meanwhile, the pharmaceutical composition also has better properties in terms of production process, such as good grindability and compressibility.

In addition, the inventors have also found surprisingly that by using a vinylpyrrolidone-vinyl acetate copolymer of a certain ratio and an enteric polymer such as HPMCAS in combination as a mixed carrier material, not only the solubility of posaconazole in gastrointestinal tract is further increased, but also the problem of precipitation or crystallization due to the significant decrease of solubility resulting from the pH change upon entry of posaconazole dissolved in stomach into intestinal tract through gastric emptying is ameliorated, thereby further increasing the absorption of posaconazole and the bioavailability thereof.

Also, the inventors have found surprisingly that by adding D-α-tocopherol polyethylene glycol 1000 succinate (TPGS) into the pharmaceutical composition, not only the solubility of posaconazole in gastrointestinal tract is further increased, but also the problem of precipitation or crystallization due to the significant decrease of solubility resulting from the pH change upon entry of posaconazole dissolved in stomach into intestinal tract through gastric emptying is ameliorated, thereby further increasing the absorption of posaconazole and the bioavailability thereof. In addition, when preparing the pharmaceutical composition using the hot melt extrusion process according to the invention, the addition of TPGS lowers the glass transition temperature (Tg) of the pharmaceutical composition, significantly decreasing the torque of the extruder, reducing energy consumption, and increasing productivity.

In particular, the present invention provides a pharmaceutical composition comprising posaconazole and a carrier material, wherein the carrier material comprises a vinylpyrrolidone-vinyl acetate copolymer or a polymer containing ethylene glycol units.

In an embodiment of the invention, posaconazole is dissolved in or dispersed at a molecular level in the carrier material.

The vinylpyrrolidone-vinyl acetate copolymer can be prepared by, e.g., free-radical polymerization of N-vinylpyrrolidone and vinyl acetate in 2-propanol. The vinylpyrrolidone-vinyl acetate copolymer can also be a copolymer of vinylpyrrolidone and vinyl acetate in a weight ratio of 15:85 to 40:60 disclosed in e.g. U.S. Pat. No. 5,426,163A.

The weight ratio of vinylpyrrolidone units to vinyl acetate units in the vinylpyrrolidone-vinyl acetate copolymer useful as a carrier material in the present invention is in the range of about 1:9 to about 9:1, preferably about 4:6 to about 6:4. The K value of the copolymer is in the range of about 25 to about 70. K value, also referred to as Fikentscher K value, is a measure of molecular weight of a polymer comprising vinylpyrrolidone units or of mixtures of such polymers commonly known in the art, and can be determined using a 1 wt. % aqueous solution according to the method described in H. Fikentscher, Cellulose-Chemie, 1932, 13:58-64/71-74. In an embodiment, the vinylpyrrolidone-vinyl acetate copolymer used in the present invention can also be, but is not limited to, e.g., Kollidon® VA64 commercially available from BASF, and/or Plasdone® S630 commercially available from International Specialty Products (both are copolymers of vinylpyrrolidone and vinyl acetate in a weight ratio of 6:4). In a preferred embodiment of the invention, the carrier material is Kollidon® VA64 (hereinafter simply referred to as VA64).

A polymer containing ethylene glycol units useful as a carrier material in the present invention can be, e.g., a polyethylene glycol/N-vinylcaprolactam/vinyl acetate copolymer, and can be, e.g., Soluplus® commercially available from BASF. In a preferred embodiment of the invention, the carrier material is Soluplus®.

In another embodiment of the invention, the carrier material further comprises one or more enteric polymers selected from the group consisting of cellulose acetate phthalate, cellulose acetate trimellitate, cellulose acetate succinate, methyl cellulose phthalate, ethylhydroxymethylcellulose phthalate, hydroxypropylmethylcellulose phthalate, hydroxypropylmethyl cellulose acetate succinate (HPMCAS), hydroxypropylmethyl cellulose acetate maleate, hydroxypropylmethylcellulose trimellitate, carboxymethylethyl cellulose, polyvinyl butyrate phthalate, polyvinyl acetate phthalate, a methacrylic acid/ethyl acrylate copolymer (wherein the preferred weight ratio of methacrylic acid to ethyl acrylate is in the range of 1:99 to 99:1) and a methacrylic acid/methyl methacrylate copolymer (wherein the preferred weight ratio of methacrylic acid to methyl methacrylate is in the range of 1:99 to 99:1), preferably selected from the group consisting of hydroxypropylmethylcellulose phthalate, HPMCAS, hydroxypropylmethyl cellulose acetate maleate and hydroxypropylmethylcellulose trimellitate, and more preferably is HPMCAS.

HPMCAS is a cellulose derivative, and has (1) two types of ether substituents: methyl and 2-hydroxypropyl, and (2) two types of ester substituents: acetyl and succinyl. In scientific literatures, it is referred to as O-(2-hydroxypropyl)-O-methyl-cellulose acetate succinate. In some embodiments, the HPMCAS is preferably at least one or more of: (i) an HPMCAS having an average acetyl content of 5-9 wt. % and an average succinyl content of 14-18 wt. %, based on the weight of the HPMCAS; (ii) an HPMCAS having an average acetyl content of 7-11 wt. % and an average succinyl content of 10-14 wt. %, based on the weight of the HPMCAS; and (iii) an HPMCAS having an average acetyl content of 10-14 wt. % and an average succinyl content of 4-8 wt. %, based on the weight of the HPMCAS, with (ii) being preferred. The HPMCAS can be, e.g., but is not limited to, AQOAT® AS-L, AQOAT® AS-M and AQOAT® AS-H commercially available from Shin-Etsu, and AquaSolve™ L, AquaSolve™ LM, AquaSolve™ LH and AquaSolve AS™ L, AquaSolve AS™ M, AquaSolve AS™ H commercially available from Ashland. In a preferred embodiment of the invention, the HPMCAS is preferably AQOAT® AS-M.

In another embodiment of the invention, the weight ratio of posaconazole to the carrier material can be in the range of about 1:1 to about 1:10, preferably about 1:1 to about 1:5, and more preferably about 1:3.

In a further embodiment of the invention, the vinylpyrrolidone-vinyl acetate copolymer or the polymer containing ethylene glycol units is present in an amount of 10 wt. % to 100 wt. %, preferably 25 wt. % to 100 wt. %, more preferably 25 wt. % to 50 wt. %, even more preferably 20 wt. % to 40 wt. %, and most preferably 25 wt. % to 37.5 wt. %, based on the total weight of the vinylpyrrolidone-vinyl acetate copolymer or the polymer containing ethylene glycol units and the enteric polymer such as HPMCAS, and each of the sub-ranges within the above ranges, e.g. any range defined by any two of the following values: 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5 and 50.

In a further embodiment of the invention, the pharmaceutical composition further comprises D-α-tocopherol polyethylene glycol 1000 succinate (TPGS, Vitamin E TPGS, Tocophersolan).

The TPGS useful in the present invention is a soluble derivative of vitamin E formed by esterification of a carboxyl group in D-α-tocopherol succinate (YES) and polyethylene glycol 1000 (PEG 1000), has a relative molecular weight of about 1513, and has been recorded in U.S. pharmacopeia. TPGS acts as a solubilizing agent in the pharmaceutical composition and pharmaceutical formulation of the present invention, and can reduce drug efflux by the effect thereof on drug transport glycoproteins in intestinal mucous cells, thus contributing to the improvement of oral bioavailability. Exemplary TPGS useful in the present invention is, but is not limited to, Kolliphor™ TPGS commercially available from BASF. In a preferred embodiment of the invention, the TPGS is Kolliphor™ PGS.

The amount of TPGS used in the present invention is not particularly limited, and can be adjusted according to actual practice. Typically, TPGS is present in an amount of about 1-12 wt. %, based on the total weight of posaconazole, the carrier material and TPGS.

The pharmaceutical composition according to the invention can further comprise one or more pharmaceutically acceptable excipients, including but not limited to, one or more of a surfactant, a pH modifier, a diluent, a disintegrant, a binder, and a lubricant.

In another aspect, the present invention also provides a method for the preparation of a pharmaceutical composition of the present invention, including but not limited to, a hot melt extrusion process and a spray drying process. For example, the specific steps of a hot melt extrusion process are:

preheating a hot melt extruder to 120° C.-180° C.;

feeding a homogeneously-mixed stoichiometric mixture of posaconazole, a carrier material, and optionally one or more pharmaceutically acceptable excipients (or a homogeneously-mixed stoichiometric mixture of posaconazole, a carrier material, TPGS, and optionally one or more pharmaceutically acceptable excipients) into the hot melt extruder, or stoichiometrically feeding posaconazole, a carrier material, and optionally one or more pharmaceutically acceptable excipients (or posaconazole, a carrier material, TAGS, and optionally one or more pharmaceutically acceptable excipients) into the hot melt extruder directly;

extruding; and cooling, pulverizing and sieving the extrudate, optionally mixing it with one or more pharmaceutically acceptable excipients, thereby obtaining the pharmaceutical composition.

The cooling process in the preparation method of the present invention is not particularly limited, and can include air cooling, water cooling, mechanical cooling, etc.

The extruder useful in the present invention is not particularly limited, and includes but is not limited to a single-screw type hot melt extruder or a twin-screw type hot melt extruder. In an embodiment of the invention, the extruder for the preparation of the pharmaceutical composition according to the invention is a twin-screw type extruder. In this case, the rotation type of the screw is not particularly limited, and includes but is not limited to co-rotating twin-screw type, counter-rotating twin-screw type, and conical twin-screw type. In a preferred embodiment of the invention, the extruder for the preparation of the pharmaceutical composition according to the invention is preferably a co-rotating twin-screw extruder.

The temperature of the hot melt extruder is set in the range of about 120° C. to about 180° C., and the rotation speed of the screw is set in the range of about 50 to about 500 rpm. The length to diameter ratio (L/D) of the screw can be about 15 to about 40. If the temperature of the hot melt extruder is too low, the L/D is too short, or the rotation speed is too slow, insufficient provision of heat energy and mechanical energy during the hot-melt process will occur, and in turn posaconazole, the carrier material or D-α-tocopherol polyethylene glycol 1000 succinate cannot get a molten state, or posaconazole cannot be dissolved in the molten carrier material, thus no single-phase solid dispersion wherein posaconazole is dissolved in or dispersed at a molecular level in the carrier material (a solid solution) can be obtained even though posaconazole is well mixed with the carrier material. If the temperature of the hot melt extruder is too high, the L/D is too long, or the rotation speed is too fast, excess provision of heat energy and mechanical energy during the hot-melt process will occur, and unnecessary degradation of posaconazole and/or the carrier material and/or TPGS will occur even though a single-phase solid dispersion wherein posaconazole is dissolved in or dispersed at a molecular level in the carrier material (a solid solution) is obtained.

In addition, the present invention provides a pharmaceutical formulation comprising a pharmaceutical composition of the present invention. In other words, a pharmaceutical composition of the present invention can be further combined with one or more pharmaceutically acceptable excipients as required to form various dosage forms. In an embodiment of the invention, the pharmaceutical formulation can be in the form of a powder, a granule, a pill, a capsule, or a tablet.

The pharmaceutically acceptable excipients include, but are not limited to, one or more of a surfactant, a pH modifier, a diluent, a disintegrant, a binder, and a lubricant.

It should be noted that the pharmaceutically acceptable excipients listed above are only illustrative and representative, and are in no way exhaustive. Therefore, the present invention is not limited by the pharmaceutically acceptable excipients illustrated hereinafter.

The surfactant used in the present invention can be an anionic, cationic, zwitterionic or nonionic surfactant, preferably a zwitterionic or nonionic surfactant. The surfactant used in the present invention can also be a mixture of two or more surfactants. The selection of the surfactant can depend on the special compound used in the pharmaceutical composition of the present invention. Surfactants useful for the pharmaceutical composition of the present invention are listed below.

A surfactant useful in the present invention is one or more of a polyoxyethylene castor oil derivative, such as polyoxyethylene glyceryl triricinoleate or polyoxyl 35 castor oil (Cremophor EL, BASF), or polyoxyethylene glyceryl hydroxyl stearate such as polyethylene glycol 40 hydrogenated castor oil (Cremophor RH40) or polyethylene glycol 60 hydrogenated castor oil (Cremophor RH 60); a block copolymer of ethylene oxide and propylene oxide, also referred to as a polyoxyethylene polyoxypropylene block copolymer or polyoxyethylene polypropylene glycol, such as Poloxamer 124, Poloxamer 188, Poloxamer 237, Poloxamer 388, Poloxamer 407 (BASF); fatty acid monoester of polyoxyethylene(20)sorbitan, such as polyoxyethylene(20) sorbitan monooleate (Tween 80), polyoxyethylene(20)sorbitan monostearate (Tween 60), polyoxyethylene(20)sorbitan monopalmitate (Tween 40), polyoxyethylene(20) sorbitan monolaurate (Tween 20); a fatty acid ester of polyethylene glycol, such as PEG-200 monolaurate, PEG-200 dilaurate, PEG-300 dilaurate, PEG-400 dilaurate, PEG-300 distearate, PEG-300 dioleate; a fatty acid monoester of alkylene glycol, such as propylene glycol monolaurate (Lauroglycol); a fatty acid monoester of sorbitan, such as sorbitan monolaurate (Span 20), sorbitan monooleate, sorbitan monopalmitate (Span 40), or sorbitan stearate.

Preferably, the surfactant useful in the present invention is a polyoxyethylene castor oil derivative, a block copolymer of ethylene oxide and propylene oxide, particularly Cremophor RH40 and/or Poloxamer 188.

A suitable pH modifier useful in the present invention is one or more of citric acid, acetic acid, fumaric acid, maleic acid, tartaric acid, malic acid, succinic acid, fumaric acid, oxalic acid, malonic acid, benzoic acid, mandelic acid, and ascorbic acid, preferably citric acid.

A suitable diluent useful in the present invention can be one or more of microcrystalline cellulose, starch, pregelatinized starch, lactose, mannitol, and calcium hydrogen phosphate.

A suitable disintegrant useful in the present invention can be one or more of low-substituted cellulose, carboxymethyl cellulose, sodium carboxymethyl cellulose, crosslinked sodium carboxymethyl cellulose, calcium carboxymethyl cellulose, sodium carboxymethyl starch, crosslinked polyvinylpyrrolidone (i.e. crospovidone), low-substituted hydroxypropylcellulose having 5-16 wt. % of hydroxypropoxy groups (L-HPC), and hydroxymethyl starch.

A suitable binder useful in the present invention can be one or more of sodium carboxymethylcellulose, hydroxypropylcellulose, methyl cellulose, ethyl cellulose, and hydroxypropylmethyl cellulose.

A suitable lubricant useful in the present invention can be one or more of magnesium stearate, silicon dioxide, talc, stearic acid, and hydrogenated vegetable oil.

EXAMPLES

The assays for the evaluation of physical and chemical properties in each example are as follows:

1. Glass Transition Temperature (Tg):

Precisely weighting about 3 mg test substance (the API posaconazole, hereinafter simply referred to as API; a drug-loaded composition (i.e. a pharmaceutical composition according to the invention); or a blank composition) and performing differential scanning calorimetry (mDSC, TA Q2000 differential scanning calorimeter) in a scanning temperature range of 40 to 180° C.

2. Powdery X-ray Diffraction (X-RD):

Taking an appropriate amount of test substance (API, a drug-loaded composition, or a blank composition), and recording the X-ray diffraction spectrum under the conditions of Cu target, voltage=45 kv, and current=45 mA (X-ray diffractometer, model D8ADVANCE, manufactured by BRUKER).

3. Apparent Solubility:

Weighting an excess amount of posaconazole pharmaceutical composition into a container, adding phosphate buffer solution (pH 6.8, about ⅔ of the volume of the container), and then placing the container in a shaking table at 37° C., and shaking for 3 h. Filtering the content with a 0.45 μm filter membrane, collecting the filtrate, diluting it with an appropriate amount of methanol, vortex mixing, and then determining the concentration of posaconazole via the following HPLC method:

| Column | $C_{18}$ column (3 μm, 4.6 × 75 mm) |
|---|---|
| Mobile phase | 0.1% phosphoric acid/acetonitrile = 50:50 |
| Flow rate | 1.5 ml/min |
| Sample plate | Room temperature |
| Detection wavelength | 254 nm |
| Injection volume | 10 μl |
| Analysis period for an injection | about 2 min |

4. Dissolution Rate:

| Dissolution method | USP II method (paddle method) |
|---|---|

-continued

| Dissolution medium | Medium of pH 1.2/6.8: 900 ml.<br>Medium of pH 1.2→6.8: after sampling at 30 min, adding 100 ml of buffer solution immediately into 800 ml of the dissolution medium of pH 1.2, such that the pH value of the overall dissolution medium reaches 6.8. |
|---|---|
| Rotary speed | 100 rpm |
| Temperature | 37.5° C. |
| Test dosage | 100 mg (posaconazole)/cup |

Analytical method for dissolution samples: the same as the HPLC method in the above assay of apparent solubility.

Example 1

Posaconazole—Kollidon® VA64 Pharmaceutical Compositions

1. Preparation:

The composition of the posaconazole—Kollidon® VA64 pharmaceutical compositions and the amount of each component are shown in Table 1-1.

Preparation Process:

Posaconazole and a carrier material and/or TPGS in the amounts shown in Table 1-1 were fed into the loading hopper of a co-rotating twin-screw extruder (Omicron 12, Steer, India) directly or after homogeneously mixed in a mixer. The temperature of the co-rotating twin-screw extruder was kept in the range of about 120° C. to about 180° C., and extrusion was carried out at a screw rotary speed of about 50 to about 500 rpm. The resulting extrudate was cooled, pulverized and sieved to obtain solid powders. Then, other pharmaceutical excipients in the amounts shown in Table 1-1 and the solid powders were homogeneously mixed, offering the posaconazole—Kollidon® VA64 pharmaceutical composition.

TABLE 1-1

Composition of posaconazole - Kollidon ® VA64 pharmaceutical compositions and amount of each component (wt. %)

|  | Function | Composition 1-1 | Composition 1-2 | Composition 1-3 | Composition 1-4 |
|---|---|---|---|---|---|
| Posaconazole | Active ingredient | 13.6 | 12.4 | 11.3 | 4.5 |
| Kollidon ® VA64 | Carrier | 13.6 | 37.3 | 33.9 | 22.7 |
| Kolliphor ® TPGS | Solubilizing agent | / | / | 4.5 | / |
| Microcrystalline cellulose | Diluent | 54.4 | 31.1 | 31.1 | 54.4 |
| Crospovidone | Disintegrant | 16.3 | 18.6 | 18.6 | 16.3 |
| Silicon dioxide | Lubricant | 1.4 | 0.4 | 0.4 | 1.4 |
| Magnesium stearate | Lubricant | 0.7 | 0.2 | 0.2 | 0.7 |

2. Evaluation of Physical and Chemical Properties 2.1. Determination of Glass Transition Temperature (Tg)

It was determined that the melting temperature of the API posaconazole (crystalline form) was about 170° C., the Tg value of Composition 1-2 was 97.6° C., the Tg value of Composition 1-3 was 71.8° C., the Tg value of the blank composition corresponding to Composition 1-2 was 106.3° C., and the Tg value of the blank composition corresponding to Composition 1-3 was 81.4° C. There were significant shifts in the Tg values of Compositions 1-2 and 1-3 by comparison with the Tg values of the two blank compositions, but they both were significantly different from the Tg value of posaconazole (68° C.), and the melting peak of posaconazole disappeared. The above results clearly show that in each of the pharmaceutical compositions of the present invention, posaconazole is dissolved in or dispersed at a molecular level in the carrier material.

2.2. Determination of Apparent Solubility

TABLE 1-2

Apparent solubility of posaconazole - Kollidon ® VA64 pharmaceutical compositions in a phosphate buffer solution, pH 6.8

|  | API | Composition 1-1 | Composition 1-2 | Composition 1-3 | Composition 1-4 |
|---|---|---|---|---|---|
| Apparent solubility (µg/ml) | <1 | 10.6 | 14.3 | 44.3 | 15.9 |
| Apparent solubility ratio (composition/API) | 1 | >10 | >14 | >44 | >15 |

It can be seen from Table 1-2 that each of the pharmaceutical compositions of the present invention prepared using a hot melt extrusion process has a significant solubilizing effect on posaconazole, demonstrating that Kollidon® VA64 has a good solubilizing effect on posaconazole. When the weight ratio of the carrier material (Kollidon® VA64) to API in the pharmaceutical composition was adjusted from 1:1 to 5:1, the apparent solubility increased from 10.6 µg/ml to 15.9 µg/ml, demonstrating that the weight ratio of the carrier material to API does not have significant influence on the solubility of posaconazole. However, addition of a small amount of Kolliphor® TPGS in Composition 1-2 led to an increase of apparent solubility from 14.3 µg/ml to 44.3 µg/ml (Composition 1-3), demonstrating that a pharmaceutical composition comprising TPGS can increase the solubility of posaconazole significantly.

2.3. Determination of Dissolution under a Stimulated In Vivo Condition

It was reported that the pH value in human stomach was about 1.2, and that in human intestine was about 6.8. The dissolution of each of the pharmaceutical compositions of the present invention was determined under a stimulated in vivo condition, and the results are shown in Table 1-3.

TABLE 1-3

Dissolution of posaconazole - Kollidon ® VA64 pharmaceutical compositions in a medium conversion of pH 1.2→6.8

| | Dissolution (%) | | | | | |
|---|---|---|---|---|---|---|
| | pH 1.2 | | | pH 6.8 | | |
| | 5 min | 10 min | 30 min | 60 min | 120 min | 180 min |
| API | 89.0 | 87.0 | 98.7 | 7.1 | 5.6 | 5.6 |
| Composition 1-1 | 36.4 | 72.3 | 87.8 | 92.1 | 66.3 | 64.8 |
| Composition 1-2 | 82.3 | 86.8 | 91.1 | 93.3 | 95.6 | 97.9 |
| Composition 1-3 | 90.1 | 91.2 | 93.3 | 94.4 | 93.0 | 95.8 |
| Composition 1-4 | 70.7 | 102.5 | 84.4 | 50.1 | 60.1 | 82.2 |

It can be seen from Table 1-3 that the dissolution of API significantly decreases from 98.7% to 5.6% upon the conversion of pH 1.2 to pH 6.8, demonstrating that posaconazole precipitates or crystallizes out from physiological fluids upon entry into intestinal tract through gastric emptying, decreasing the in vivo bioavailability thereof. The dissolution decrease of the pharmaceutical compositions of the present invention (especially Composition 1-2 and Composition 1-3) is not significant within 3 h from the conversion of pH 1.2 to pH 6.8 by comparison with API Further, at each time point after 30 min, the dissolution of each of the pharmaceutical compositions of the present invention is above 50%, and up to 97.9%, significantly higher than the dissolution of API, demonstrating that they all can improve the absorption of posaconazole in vivo significantly. In particular, at each time point after 30 min, the dissolution of both Composition 1-2 and Composition 1-3 is above 93%, demonstrating that they can improve the absorption of posaconazole in vivo better.

Example 2

Posaconazole—Kollidon® VA64/HPMCAS Pharmaceutical Compositions (Pharmaceutical Compositions Having Mixed Carriers)

1. Preparation:

The composition of the posaconazole—Kollidon® VA64/HPMCAS pharmaceutical compositions and the amount of each component are shown in Table 2-1.

Preparation Process:

Posaconazole and a carrier material (VA64 and/or HPMCAS (in particular, AQOAT® AS-M)) and/or TPGS in the amounts shown in Table 2-1 were fed into the loading hopper of a co-rotating twin-screw extruder (Omicron 12, Steer, India) directly or after homogeneously mixed in a mixer. The temperature of the co-rotating twin-screw extruder was kept in the range of about 120° C. to about 180° C., and extrusion was carried out at a screw rotation speed of about 50 to about 500 rpm. The resulting extrudate was cooled, pulverized and sieved to obtain solid powders. Then, other pharmaceutical excipients in the amounts shown in Table 2-1 and the solid powders were homogeneously mixed, offering the posaconazole—Kollidon® VA64/HPMCAS pharmaceutical composition.

Composition 2-1 was a comparative composition prepared according to US2011123627A, comprising only AQOAT® AS-M in its carrier material.

TABLE 2-1

Composition of posaconazole - Kollidon ® VA64/HPMCAS pharmaceutical compositions and amount of each component (wt. %)

| | Function | Composition 2-1 | Composition 2-2 | Composition 2-3 | Composition 2-4 | Composition 2-5 | Composition 2-6 |
|---|---|---|---|---|---|---|---|
| Posaconazole | Active ingredient | 17.4 | 15.6 | 12.5 | 12.5 | 14.5 | 7.9 |
| AQOAT ® AS-M | Carrier | 52.2 | 35.2 | 23.5 | 18.8 | 18.2 | 19.7 |
| Kollidon ® VA64 | Carrier | / | 11.7 | 14.1 | 18.8 | 10.9 | 11.8 |
| Kolliphor ® TPGS | Solubilizing agent | / | 6.3 | 5.0 | 5.0 | 4.3 | 3.9 |
| Microcrystalline cellulose | Diluent | 12.3 | 15.5 | 29.5 | 29.5 | 34.3 | 37.3 |
| Hydroxypropyl cellulose | Binder | 13.0 | 9.4 | / | / | / | / |
| Crosslinked sodium carboxymethyl cellulose | Disintegrant | 4.3 | 5.5 | 13.8 | 13.8 | 15.9 | 17.3 |
| Silicon dioxide | Lubricant | 0.5 | 0.5 | 1.0 | 1.0 | 1.2 | 1.3 |
| Magnesium stearate | Lubricant | 0.3 | 0.3 | 0.6 | 0.6 | 0.7 | 0.8 |

2. Evaluation of Physical and Chemical Properties
2.1. Determination of Glass Transition Temperature (Tg)

The determination results are as shown in FIG. 1. FIG. 1 shows the effect of VA64 content on Tg value in a pharmaceutical composition prepared with posaconazole—Kollidon® VA64 and/or HPMCAS carrier(s), wherein Tg values corresponding to VA64/(VA64+HPMCAS)% of 0%, 25%, 37.5%, 50% and 100% are those of Composition 2-1, Composition 2-2, Composition 2-3, Composition 2-4, and Composition 1-3 or the corresponding blank compositions, respectively. It can be seen from FIG. 1 that with the increase of VA64 content in the compositions, the Tg values tend to decrease, and the Tg values of drug-loaded compositions have significant shifts by comparison with the Tg values of the corresponding blank compositions, decreasing by about 10-20° C., though significantly differ from the Tg value of posaconazole (68° C.).

Figure 2:
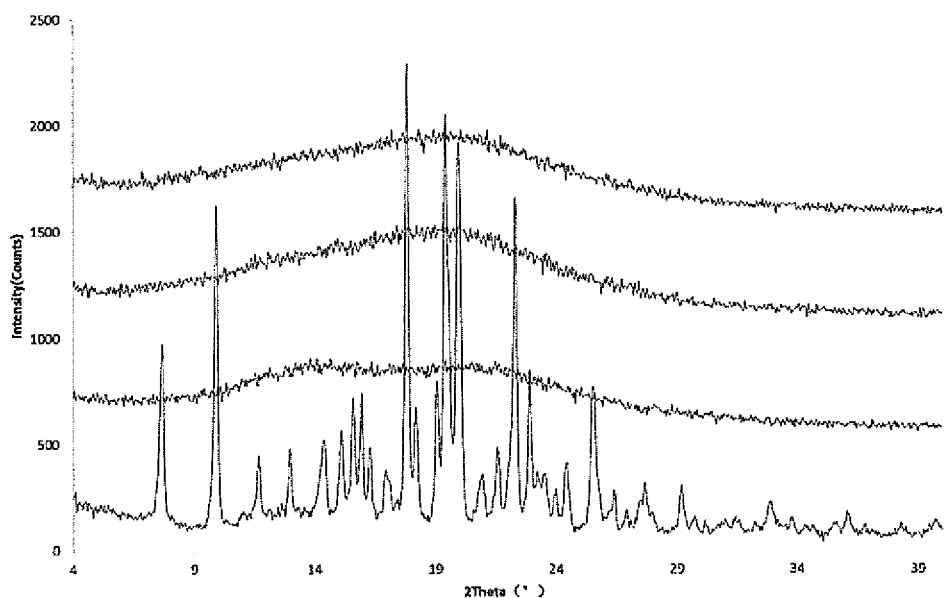
FIG. 2 shows X-RD spectrums of pharmaceutical compositions prepared with posaconazole—Kollidon® VA64 and/or HPMCAS carrier(s), which are, from bottom to top, the X-RD spectrums of API, Composition 1-3, Composition 2-3, and Composition 2-4, respectively.

FIG. 2 shows X-RD spectrums of pharmaceutical compositions prepared with posaconazole—Kollidon® VA64 and/or HPMCAS carrier(s), which are, from bottom to top, the X-RD spectrums of API, Composition 1-3, Composition 2-3, and Composition 2-4, respectively. It can be seen from FIG. 2 that no diffraction peak of posaconazole exists in the X-RD spectrums of Composition 1-3 prepared with a single carrier material and Compositions 2-3 and 2-4 prepared with a mixed carrier material, demonstrating that in the pharmaceutical composition of the present invention, posaconazole is dissolved in or dispersed at a molecular level in the carrier material.

2.2. Determination of Apparent Solubility

TABLE 2-2

Apparent solubility of posaconazole - Kollidon ® VA64/HPMCAS pharmaceutical compositions in a phosphate buffer solution, pH 6.8

|  | API | Composition 2-1 | Composition 2-2 | Composition 2-3 | Composition 2-4 | Composition 2-5 | Composition 2-6 |
|---|---|---|---|---|---|---|---|
| Apparent solubility (µg/ml) | <1 | 90.1 | 92.6 | 93.7 | 68.3 | 119.8 | 116.3 |
| Apparent solubility ratio (composition/API) | 1 | >90 | >92 | >93 | >68 | >119 | >116 |

It can be seen from Table 2-2 that each of the pharmaceutical compositions of the present invention having mixed carriers and prepared using a hot melt extrusion process has a significant solubilizing effect on posaconazole. When the weight ratio of API to the carrier material was kept constant (e.g., 1:3), adjusting VA64/(VA64+HPMCAS)% from 100% (Composition 1-3) to 50% (Composition 2-4) led to an increase of the apparent solubility from 44.3 µg/ml to 68.3 µg/ml, and further adjusting VA64/(VA64+HPMCAS)% from 50% to 37.5% (Composition 2-3) led to a further increase of the apparent solubility from 68.3 µg/ml to 93.7 µg/ml, but further decreasing VA64/(VA64+HPMCAS)% to 0% (Composition 2-1) led to a slight decrease of the apparent solubility to 90.1 µg/ml, demonstrating that pharmaceutical compositions prepared with a mixed carrier material had an advantageous effect on the solubility of posaconazole in a certain range. As shown in Table 2-2, Composition 2-5 increases the solubility of posaconazole most significantly.

On the other hand, when VA64/(VA64+HPMCAS)% in the carrier material was kept constant (e.g., 37.5%), adjusting the weight ratio of API to the carrier material from 1:2 (Composition 2-5) to 1:3 (Composition 2-3) and 1:4 (Composition 2-6) led to increase of the apparent solubility of the pharmaceutical composition of at least 119, 93, and 116 times of that of API, respectively, and they were all higher than the apparent solubility of the comparative composition (Composition 2-1), demonstrating that the compositions having VA64/(VA64+HPMCAS)% of 37.5% in the mixed carrier material had the most significant solubilizing effects on posaconazole.

2.3 Determination of Dissolution Under a Stimulated In Vivo Condition

TABLE 2-3

Dissolution of posaconazole - Kollidon ® VA64/HPMCAS pharmaceutical composition in a medium conversion of pH 1.2→6.8

| | Dissolution (%) | | | | | |
|---|---|---|---|---|---|---|
| | pH 1.2 | | | pH 6.8 | | |
| | 5 min | 10 min | 30 min | 60 min | 120 min | 180 min |
| API | 89.0 | 87.0 | 98.7 | 7.1 | 5.6 | 5.6 |
| Composition 2-1 | 2.0 | 4.2 | 5.6 | 95.2 | 92.9 | 92.0 |
| Composition 2-2 | 62.3 | 70.5 | 77.6 | 103.0 | 99.6 | 103.1 |
| Composition 2-3 | 72.6 | 79.7 | 85.2 | 93.0 | 95.4 | 94.2 |
| Composition 2-4 | 84.7 | 87.1 | 91.0 | 95.9 | 94.7 | 96.4 |
| Composition 2-5 | 63.4 | 65.4 | 71.4 | 83.1 | 83.0 | 84.1 |
| Composition 2-6 | 85.0 | 87.6 | 100.1 | 101.0 | 95.7 | 100.3 |

Figure 3:
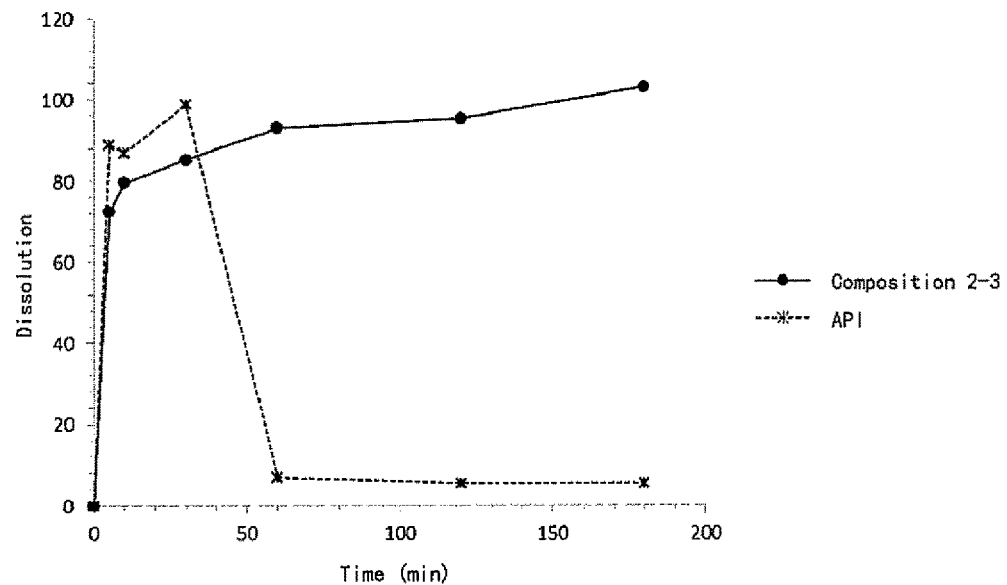
FIG. 3 shows dissolution profiles of a pharmaceutical composition (Composition 2-3) prepared with posaconazole—Kollidon® VA64/HPMCAS mixed carriers, and of API, under a simulated in vivo fasted condition with a pH conversion of from 1.2 to 6.8 at the time of 30 min.

The dissolution profiles of Composition 2-3 and API are shown in FIG. 3. It can be seen from Table 2-3 and FIG. 3 that the dissolution of API significantly decreases from 98.7% to 5.6% upon the conversion of pH 1.2 to pH 6.8, demonstrating that posaconazole precipitates or crystallizes out from physiological fluids upon entry into intestinal tract through gastric emptying, decreasing the in vivo bioavailability thereof. The dissolution decrease of the pharmaceutical compositions of the present invention is not significant within 3 h from the conversion of pH 1.2 to pH 6.8 by comparison with API, and at each time point after 30 min, the dissolution of Compositions 2-2 to 2-6 are above 83%, demonstrating that they can improve the absorption of posaconazole in vivo significantly. At pH 1.2, the dissolution of Compositions 2-2 to 2-6 prepared with a mixed carrier material is significantly improved by comparison with Composition 2-1 prepared with a single carrier material, demonstrating that the absorption of Compositions 2-2 to 2-6 in stomach will be better than that of Composition 2-1. At pH 6.8, the dissolution of Compositions 2-2 to 2-6 prepared with a mixed carrier material is close to that of Composition 2-1 prepared with a single carrier material, demonstrating that the absorption of Compositions 2-2 to 2-6 in intestinal tract will be comparable to that of Composition 2-1. Therefore, the overall absorption of Compositions 2-2 to 2-6 prepared with a mixed carrier material in vivo will be better than that of Composition 2-1.

Figure 4:
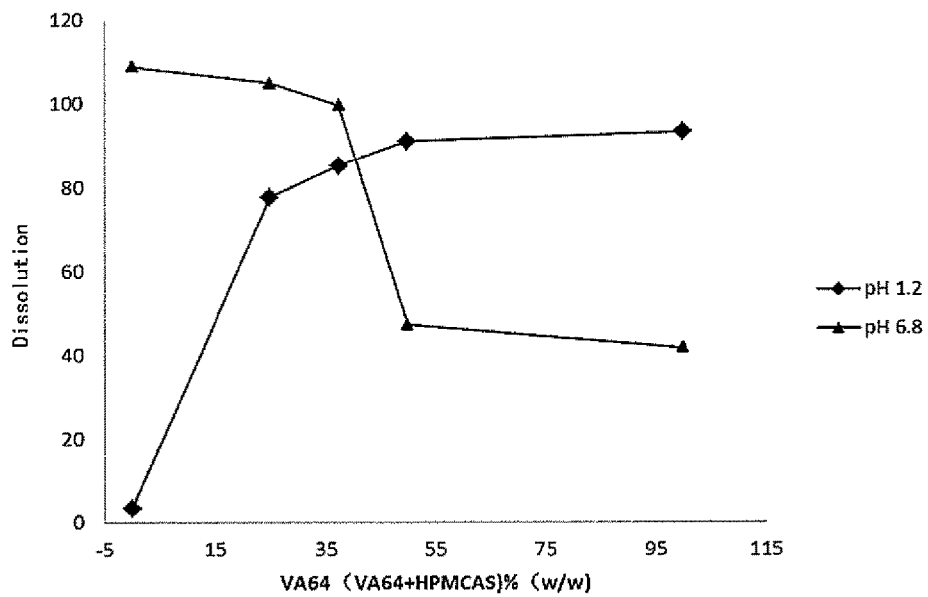
FIG. 4 shows the effect of VA64 content in a pharmaceutical composition (wherein the weight ratio of posaconazole to the carrier material is 1:3) prepared with posaconazole—Kollidon® VA64 and/or HPMCAS carrier(s) on the dissolution of posaconazole in dissolution mediums of pH 1.2 and pH 6.8, wherein the dissolution values corresponding to VA64/(VA64+HPMCAS)% of 0%, 25%, 37.5%, 50% and 100% are those of Composition 2-1, Composition 2-2, Composition 2-3, Composition 2-4 and Composition 1-3, respectively.

FIG. 4 shows the effect of VA64 content in a pharmaceutical composition (wherein the weight ratio of posaconazole to the carrier material is 1:3) prepared with posaconazole—Kollidon® VA64 and/or HPMCAS carrier(s) on the dissolution of posaconazole in dissolution mediums at pH 1.2 and pH 6.8, wherein dissolution corresponding to VA64/(VA64+HPMCAS)% of 0%, 25%, 37.5%, 50% and 100% is that of Composition 2-1, Composition 2-2, Composition 2-3, Composition 2-4, and Composition 1-3, respectively. It can be seen from FIG. 4 that under a dissolution condition of pH 1.2, the dissolution of each of the pharmaceutical compositions is above 75% when VA64/(VA64+HPMCAS)% is above 25.0%, significantly higher than that of Composition 2-1 wherein VA64/(VA64+HPMCAS)% is 0%, and under a dissolution condition of pH 6.8, the dissolution of each of the pharmaceutical compositions decreases to lower than 50% when VA64/(VA64+HPMCAS)% increases to higher than 50.0%.

The above results show that the overall dissolution of Composition 2-2 and Composition 2-3 prepared with mixed carrier materials having VA64/(VA64+HPMCAS)% of 25.0% and 37.5%, respectively in the dissolution mediums at the two pH values is significantly better than that of Composition 2-1 comprising no VA64 and Composition 1-3 comprising VA64 solely.

Example 3

Posaconazole—Soluplus® Pharmaceutical Compositions

1. Preparation:

The composition of posaconazole—Soluplus® pharmaceutical compositions and the amount of each component are shown in Table 3-1.

TABLE 3-1

Composition of posaconazole - Soluplus ® pharmaceutical compositions and amount of each component (wt. %)

| | Function | Composition 3-1 | Composition 3-2 | Composition 3-3 |
|---|---|---|---|---|
| Posaconazole | Active ingredient | 14.3 | 7.2 | 4.8 |
| Soluplus ® | Carrier | 14.3 | 21.7 | 24.2 |
| Microcrystalline cellulose | Diluent | 57.2 | 58.1 | 58.0 |
| Crosslinked sodium carboxymethyl cellulose | Disintegrant | 12.1 | 10.9 | 10.9 |
| Silicon dioxide | Lubricant | 1.4 | 1.4 | 1.4 |
| Magnesium stearate | Lucricant | 0.7 | 0.7 | 0.7 |

Preparation Process:

Posaconazole and a carrier material in the amounts shown in Table 3-1 were fed into the loading hopper of a co-rotating twin-screw extruder (Omicron 12, Steer, India) directly or after homogeneously mixed in a mixer. The temperature of the co-rotating twin-screw extruder was kept in the range of about 120° C. to about 180° C., and extrusion was carried out at a screw rotation speed of about 50 to about 500 rpm. The resulting extrudate was cooled, pulverized and sieved to obtain solid powders. Then, other pharmaceutical excipients in the amounts shown in Table 3-1 and the solid powders were homogeneously mixed, offering the posaconazole—Soluplus® pharmaceutical composition.

2. Evaluation of Physical and Chemical Properties
2.1. Determination of Apparent Solubility

TABLE 3-2

Apparent solubility of posaconazole - Soluplus ® pharmaceutical compositions in a phosphate buffer solution, pH 6.8

| | API | Composition 3-1 | Composition 3-2 | Composition 3-3 |
|---|---|---|---|---|
| Apparent solubility (µg/ml) | <1 | 40.9 | 87.7 | 159.0 |
| Apparent solubility ratio (composition/API) | 1 | >40 | >87 | >159 |

It can be seen from Table 3-2 that each of the posaconazole—Soluplus® pharmaceutical compositions can improve the solubility of posaconazole significantly, and with the increase of the weight proportion of the carrier material, the solubilizing effect becomes more and more apparent. When the weight ratio of the carrier material to API is 5:1 (Composition 3-3), the solubility of posaconazole can be increased by at least 159 times.

2.2. Determination of Dissolution Under a Stimulated In Vivo Condition

TABLE 3-3

Dissolution of posaconazole - Soluplus ® pharmaceutical compositions in a medium conversion of pH 1.2→6.8

| | Dissolution (%) | | | | | |
|---|---|---|---|---|---|---|
| | pH 1.2 | | | pH 6.8 | | |
| | 5 min | 10 min | 30 min | 60 min | 120 min | 180 min |
| API | 89.0 | 87.0 | 98.7 | 7.1 | 5.6 | 5.6 |
| Composition 3-1 | 55.6 | 68.1 | 88.7 | 71.3 | 65.2 | 54.0 |
| Composition 3-2 | 67.8 | 71.5 | 101.3 | 67.9 | 45.2 | 32.9 |
| Composition 3-3 | 58.8 | 92.2 | 102.3 | 52.4 | 28.9 | 25.6 |

It can be seen from Table 3-3 that each of the posaconazole—Soluplus® pharmaceutical compositions can significantly increase the dissolution of posaconazole under a stimulated in vivo condition by comparison with API.

Example 4

Posaconazole—Soluplus®/HPMCAS Pharmaceutical Composition (Pharmaceutical Composition Having Mixed Carriers)

1. Preparation:

The composition of the posaconazole—Soluplus®/HPMCAS pharmaceutical compositions and the amount of each component are shown in Table 4-1.

TABLE 4-1

Composition of posaconazole - Soluplus ®/HPMCAS pharmaceutical compositions and amount of each component (wt. %)

| | Fuction | Composition 4-1 | Composition 4-2 | Composition 4-3 |
|---|---|---|---|---|
| Posaconazole | Active ingredient | 13.2 | 13.2 | 13.2 |
| Soluplus ® | Carrier | 29.6 | 19.8 | 10.0 |
| AQOAT ® AS-M | Carrier | 10.0 | 19.8 | 29.6 |
| Microcrystalline cellulose | Diluent | 31.2 | 31.2 | 31.2 |

TABLE 4-1-continued

Composition of posaconazole - Soluplus ®/HPMCAS pharmaceutical compositions and amount of each component (wt. %)

| | Fuction | Composition 4-1 | Composition 4-2 | Composition 4-3 |
|---|---|---|---|---|
| Crosslinked sodium carboxymethyl cellulose | Disintegrant | 14.5 | 14.5 | 14.5 |
| Silicon dioxide | Lubricant | 1.1 | 1.1 | 1.1 |
| Magnesium stearate | Lubricant | 0.7 | 0.7 | 0.7 |

Preparation Process:

Posaconazole and a mixed carrier material (Soluplus® and HPMCAS (in particular, AQOAT® AS-M)) in the amounts shown in Table 4-1 were fed into the loading hopper of a co-rotating twin-screw extruder (Omicron 12, Steer, India) directly or after homogeneously mixed in a mixer. The temperature of the co-rotating twin-screw extruder was kept in the range of about 120° C. to about 180° C., and extrusion was carried out at a screw rotation speed of about 50 to about 500 rpm. The resulting extrudate was cooled, pulverized and sieved to obtain solid powders. Then, other pharmaceutical excipients in the amounts shown in Table 4-1 and the solid powders were homogeneously mixed, offering the posaconazole—Soluplus®/HPMCAS pharmaceutical composition.

2. Evaluation of Physical and Chemical Properties 2.1. Determination of Apparent Solubility

TABLE 4-2

Apparent solubility of posaconazole - Soluplus ®/HPMCAS pharmaceutical compositions in a phosphate buffer solution, pH 6.8

| | API | Composition 4-1 | Composition 4-2 | Composition 4-3 |
|---|---|---|---|---|
| Apparent solubility (μg/ml) | <1 | 84.0 | 22.4 | 20.4 |
| Apparent solubility ratio (composition/API) | 1 | >84 | >22 | >20 |

It can be seen from Table 4-2 that each of the posaconazole—Soluplus®/HPMCAS pharmaceutical compositions can improve the solubility of posaconazole significantly, and the increase by Composition 4-1 is most significant.

2.2. Determination of Dissolution Under a Stimulated In Vivo Condition

TABLE 4-3

Dissolution of posaconazole - Soluplus ®/HPMCAS pharmaceutical compositions in a medium conversion of pH 1.2→6.8

| | Dissolution (%) | | | | | |
|---|---|---|---|---|---|---|
| | pH 1.2 | | | pH 6.8 | | |
| | 5 min | 10 min | 30 min | 60 min | 120 min | 180 min |
| API | 89.0 | 87.0 | 98.7 | 7.1 | 5.6 | 5.6 |
| Composition 4-1 | 87.6 | 93.8 | 84.9 | 74.3 | 55.6 | 52.8 |
| Composition 4-2 | 36.2 | 45.8 | 62.8 | 51.5 | 42.9 | 49.8 |
| Composition 4-3 | 10.2 | 12.5 | 25.8 | 33.6 | 20.9 | 25.4 |

It can be seen from Table 4-3 that each of the posaconazole—Soluplus®/HPMCAS pharmaceutical compositions can significantly increase the dissolution under a stimulated in vivo condition by comparison with API.

Example 5

Evaluation of Preparation Methods of Posaconazole—Kollidon® VA64/HPMCAS Pharmaceutical Compositions (Pharmaceutical Compositions Having Mixed Carriers)

1. Hot Melt Extrusion Process

TABLE 5-1

Parameters of hot melt extrusion process

| Composition | Rotation speed of material feeder (RPM) | Rotation speed of screw (RPM) | Melting temperature of material (° C.) | Energy consumption per Kg (kW · h) | Percentage torque |
|---|---|---|---|---|---|
| 1-3 | 30 | 160 | 125 | 12 | 51% |
| 2-1 | 60 | 200 | 137 | 6 | 59% |
| 2-2 | 30 | 200 | 136 | 7 | 34% |
| 2-3 | 25 | 160 | 136 | 4 | 12% |
| 2-4 | 25 | 150 | 136 | 4 | 12% |

For specific processes, see the preparation of the pharmaceutical compositions in Examples 1-4. As shown in Table 5-1, compositions prepared with a mixed carrier material have lower energy consumption per Kg and produce lower percent torque by comparison with Composition 1-3 and 2-1 prepared with a single carrier material, demonstrating that a pharmaceutical composition prepared with a mixed carrier material can significantly decrease the energy consumption and instrument torque in a hot melt extrusion process, and greatly increase the operability thereof.

2. Pulverization Process

TABLE 5-2

Parameters of extrudate pulverization process

| Composition | Weight of extrudate (g) | Pulverization period (s) | Weight of granules passing through 60 mesh sieve (g) | Sieving efficiency* w/w (%) |
|---|---|---|---|---|
| 1-3 | 20.0 | 30 | 16.5 | 82.5 |
| 2-1 | 20.3 | 30 | 1.6 | 7.9 |

TABLE 5-2-continued

Parameters of extrudate pulverization process

| Composition | Weight of extrudate (g) | Pulverization period (s) | Weight of granules passing through 60 mesh sieve (g) | Sieving efficiency* w/w (%) |
|---|---|---|---|---|
| 2-2 | 20.5 | 30 | 6.8 | 33.2 |
| 2-3 | 22.8 | 30 | 11.6 | 50.9 |
| 2-4 | 20.0 | 30 | 10.7 | 53.5 |

Note:
*means the weight ratio of granules after sieving to overall granules before sieving.

The extrudate obtained in the preparation of each pharmaceutical composition was cut into a stick of about 2 cm, and was pulverized for 30s using a small-sized coffee grinder (KG40, Delonghi, Italy). The pulverized granules were sieved using a 60 mesh sieve, the sieved powders were weighted, and the sieve efficiency was calculated. As shown in Table 5-2, a pharmaceutical composition prepared with a mixed carrier material comprising VA64 or a single carrier material VA64 has a higher sieving efficiency by comparison with the sieving efficiency (7.9%) of Composition 2-1 prepared with a single carrier material HPMCAS, demonstrating better operability of the pulverization process thereof.

3. Tableting Process

TABLE 5-3

Composition of tablet formulations (wt. %) and parameters of tableting processes

| | Composition 1-3 | Composition 2-1 | Composition 2-2 | Composition 2-3 | Composition 2-4 |
|---|---|---|---|---|---|
| Solid powders* | 55.0 | 55.0 | 55.0 | 55.0 | 55.0 |
| Crystalline cellulose | 29.6 | 29.6 | 29.6 | 29.6 | 29.6 |
| Crosslinked sodium carboxymethyl cellulose | 13.8 | 13.8 | 13.8 | 13.8 | 13.8 |
| Silicon dioxide | 1.0 | 1.0 | 1.0 | 1.0 | 1.0 |
| Magnesium stearate | 0.6 | 0.6 | 0.6 | 0.6 | 0.6 |
| Tableting pressure (cm) | 13.8 | 13.8 | 13.8 | 13.8 | 13.8 |
| Filling amounts of materials (mg) | 800 | 800 | 800 | 800 | 800 |
| Tablet hardness (kg) | 38.5 | 1.9 | 8.7 | 15.5 | 21.0 |
| Disintegrating time (min) | 21.9 | 0.3 | 0.6 | 2.0 | 3.3 |

Note:
*means the solid powders before mixed with the pharmaceutical excipients in the preparation of the compositions in Examples 1-4.

The solid powders sieved using a 60 mesh sieve and other pharmaceutical excipients in the amounts shown in Table 5-3 were homogeneously mixed, and were tableted using a single-punch tablet machine (DP-5, Shanghai Tianfan Pharmaceutical Machinery Factory) at the same pressure and the same filling amounts of materials, in order to evaluate the compressibility (hardness tester, YD-35, Tianjin Tianda Tianfa Technology Co., Ltd.) and disintegration performance (disintegration tester, ZB-1, Tianjin Tianda Tianfa Technology Co., Ltd.) of various formulations. The results are shown in Table 5-3. It can be seen from Table 5-3 that with the decrease of VA64 content in the carrier material, the hardness of the tablets decreases, and the disintegration time decreases.

Example 6

In Vivo Pharmacokinetic Study of Posaconazole—Kollidon® VA64/HPMCAS Pharmaceutical Compositions (Pharmaceutical Compositions Having Mixed Carriers)

An open, randomized, two-period, double crossover, self-control, comparative pharmacokinetic study was conducted in human subjects under fasted condition.

1. Method

The subjects were 9 healthy male subjects in the age of 20 to 45, having a body mass index (BMI) of 19 to 25. All subjects fully understood the content of the test and had signed the informed consent form voluntarily.

The subjects checked in care units for clinical trial at 18:00 and started fasting at 20:00 on day 1. On day 2, blood samples (blank samples before administration) were collected at 7:00, and Composition 2-1 or Composition 2-2 (see Example 2 for their specific composition) comprising 100 mg posaconazole were administered to the fasted subjects with 240 ml of water under the guidance of a physician at 8:00. Blood samples were collected at 1, 2, 3, 4, 5, 6, 8, 12, 24, 48, and 72 hours after administration (12 times, 3 ml/time). The blood samples were transferred to heparin anticoagulation tubes, shaken homogeneously, centrifuged for 5 min at 4000 rpm to obtain plasma samples, which were divided into two parts and stored at −20° C. for the determination of plasma drug concentration. On day 9, cross-over administration was carried out using the same method as on day 2, and then blood samples were collected in the same way. Vital signs and adverse events of the subjects were observed throughout the experiment in order to ensure their safety.

The concentration of posaconazole in each plasma sample (plasma drug concentration) was determined by a LC-MS/MS method, and was calculated by DAS 3.2.5, a statistical software for pharmacokinetics, in order to perform biological statistical analysis to get the pharmacokinetic parameters of Composition 2-1 and Composition 2-2. The ratio of arithmetic mean value of each parameter was calculated (Composition 2-2/Composition 2-1) and the distribution of 90% confidence interval of AUC and $C_{max}$ of Composition 2-2 was evaluated. The $C_{max}$, $AUC_{0-72\ h}$, and $AUC_{0-\infty}$ of Composition 2-2 and Composition 2-1 were subjected to logarithm transformation, and then subjected to variance analysis. A two one-side T test was also performed.

2. Results

Figure 5:
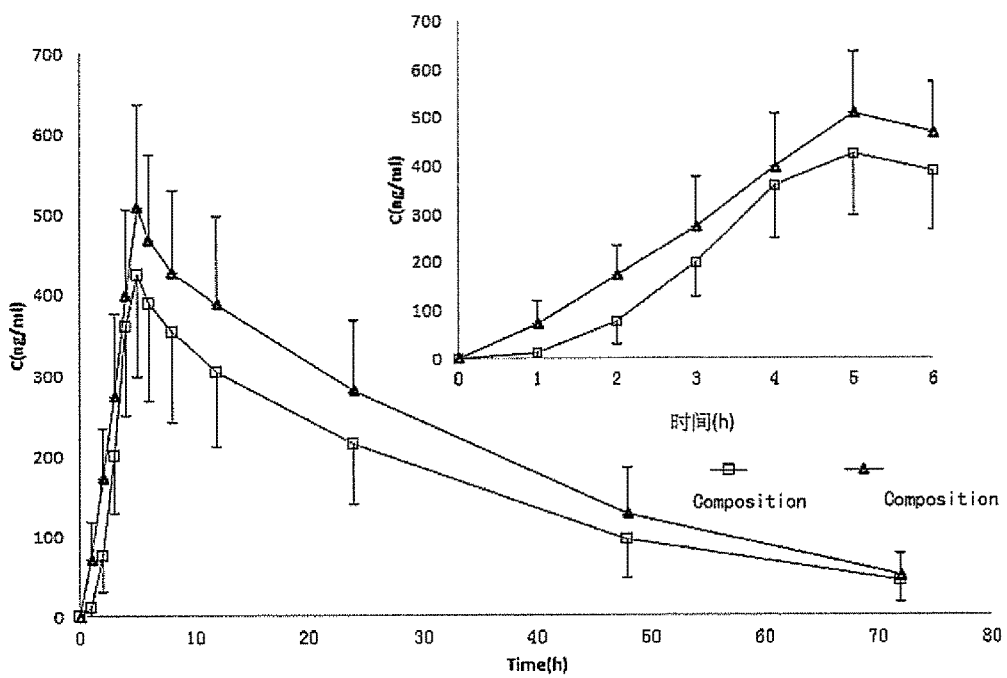
FIG. 5 shows the average plasma drug concentration—time curves of posaconazole obtained after administering pharmaceutical compositions prepared with posaconazole—Kollidon® VA64 and/or an HPMCAS carrier(s) (Composition 2-1 and Composition 2-2) to fasted human subjects, wherein VA64/(VA64+HPMCAS)% in Composition 2-1 and Composition 2-2 is 0% and 25%, respectively.

The experimental results are shown in Table 6-1 and FIG. 5. The results show that for $C_{max}$, $AUC_{0-72\,h}$, and $AUC_{0-\infty}$ of posaconazole, significant difference exists between Composition 2-1 and Composition 2-2. The 90% confidence interval of $C_{max}$ of Composition 2-2 is calculated to be (106%~147%), the 90% confidence interval of $AUC_{0-72\,h}$ is calculated to be (115.8%~147.1%), and the 90% confidence interval of $AUC_{0-\infty}$ is calculated to be (117.9%~1463%), with a sample size of n=9.

TABLE 6-1

Pharmacokinetic parameters of posaconazole

| Pharmacokinetic parameters (arithmetic mean values, n = 9) | Composition 2-1 | Composition 2-2 |
|---|---|---|
| $C_{max}$ (ng · ml$^{-1}$) | 432.8 | 533.2 |
| $AUC_{0-72\,h}$ (ng · h · ml$^{-1}$) | 11793 | 15214 |
| $AUC_{0-\infty}$ (ng · h · ml$^{-1}$) | 13251 | 17276 |

It can be seen from FIG. 5 and Table 6-1 that posaconazole in the composition having a Kollidon® VA64/HPMCAS mixed carrier material (Composition 2-2) achieves faster absorption speed, higher plasma drug concentration, and correspondingly higher bioavailability in vivo by comparison with the composition having a single carrier material HPMCAS (Composition 2-1). The ratio of arithmetic mean value of $C_{max}$ (Composition 2-2/Composition 2-1) is 1.23; the ratio of arithmetic mean value of $AUC_{0-72\,h}$ (Composition 2-2/Composition 2-1) is 1.29; and the ratio of arithmetic mean value of $AUC_{0-\infty}$ (Composition 2-2/Composition 2-1) is 1.30. The data show that on the premise of ensuring the dissolution at pH 6.8 is comparable to comparative composition 2-1, by increasing the dissolution or solubility of posaconazole under an acidic condition, the absorption of the drug in stomach in vivo is increased, and thus the absorption speed and availability of the drug in vivo are increased, such that the bioavailability of Composition 2-2 in vivo is increased.

We claim:

1. A pharmaceutical composition comprising posaconazole and a carrier material, wherein the carrier material comprises an enteric polymer and a vinylpyrrolidone-vinyl acetate copolymer or a polyethylene glycol/N-vinylcaprolactam/vinyl acetate copolymer, wherein posaconazole is dissolved in or dispersed at a molecular level in the carrier material, wherein the enteric polymer is hydroxypropylmethyl cellulose acetate succinate, and wherein the vinylpyrrolidone-vinyl acetate copolymer or the polyethylene glycol/N-vinylcaprolactam/vinyl acetate copolymer is present in an amount of 25 wt. % to 50 wt. %, based on the total weight of the vinylpyrrolidone-vinyl acetate copolymer or the polyethylene glycol/N-vinylcaprolactam/vinyl acetate copolymer and the enteric polymer.

2. The pharmaceutical composition according to claim 1, wherein the weight ratio of vinylpyrrolidone units to vinyl acetate units in the vinylpyrrolidone-vinyl acetate copolymer is in the range of 1:9 to 9:1.

3. The pharmaceutical composition according to claim 1, wherein the weight ratio of posaconazole to the carrier material is in the range of 1:1-1:5.

4. The pharmaceutical composition according to claim 1, further comprising D-α-tocopherol polyethylene glycol 1000 succinate as a solubilizing agent.

5. The pharmaceutical composition according to claim 4, wherein D-α-tocopherol polyethylene glycol 1000 succinate is present in an amount of 1-12 wt. %, based on the total weight of posaconazole, the carrier material and D-α-tocopherol polyethylene glycol 1000 succinate.

6. The pharmaceutical composition according to claim 4, further comprising one or more pharmaceutically acceptable excipients selected from the group consisting of a surfactant, a pH modifier, a diluent, a disintegrant, a binder, and a lubricant.

7. A method for the prevention and/or treatment of fungal infections and related diseases in a mammal, comprising administering an effective amount of a pharmaceutical composition according to claim 1 to the mammal.

8. A method for the preparation of a pharmaceutical composition according to claim 1, comprising:
preheating a hot melt extruder to 120° C-180° C.;
feeding a homogeneously-mixed stoichiometric mixture of posaconazole, a carrier material, and optionally one or more pharmaceutically acceptable excipients into the hot melt extruder, or stoichiometrically feeding posaconazole, a carrier material, and optionally one or more pharmaceutically acceptable excipients into the hot melt extruder directly;
extruding; and
cooling, pulverizing and sieving the extrudate, optionally mixing it with one or more pharmaceutically acceptable excipients, thereby obtaining the pharmaceutical composition.

9. A pharmaceutical formulation in the form of a powder, a granule, a pill, a capsule or a tablet, comprising the pharmaceutical composition according to claim 1.

10. The pharmaceutical composition according to claim 1, wherein the weight ratio of vinylpyrrolidone units to vinyl acetate units in the vinylpyrrolidone-vinyl acetate copolymer is in the range of 4:6 to 6:4.

11. The pharmaceutical composition according to claim 1, wherein the weight ratio of posaconazole to the carrier material is 1:3.

12. The pharmaceutical composition according to claim 1, wherein the vinylpyrrolidone-vinyl acetate copolymer or the polyethylene glycol/N-vinylcaprolactam/vinyl acetate copolymer is present in an amount of 25 wt. % to 40 wt. %, based on the total weight of the vinylpyrrolidone-vinyl acetate copolymer or the polyethylene glycol/N-vinylcaprolactam/vinyl acetate copolymer and the enteric polymer.

13. The pharmaceutical composition according to claim 1, wherein the vinylpyrrolidone-vinyl acetate copolymer or the polyethylene glycol/N-vinylcaprolactam/vinyl acetate copolymer is present in an amount of 25 wt. % to 37.5 wt. %, based on the total weight of the vinylpyrrolidone-vinyl acetate copolymer or the polyethylene glycol/N-vinylcaprolactam/vinyl acetate copolymer and the enteric polymer.

* * * * *